United States Patent [19]  [11]  4,292,219
Lyons et al.  [45]  Sep. 29, 1981

[54] LATEX-BASE PAINT CONTAINING 2-METHOXY-2-PHENYL PROPANE OR 8-METHOXY-P-MENTHANE

[75] Inventors: James E. Lyons; Peter Hosler, both of Wallingford, Pa.

[73] Assignee: Suntech, Inc., Philadelphia, Pa.

[21] Appl. No.: 101,656

[22] Filed: Dec. 10, 1979

Related U.S. Application Data

[60] Division of Ser. No. 863,569, Dec. 22, 1977, which is a continuation-in-part of Ser. No. 714,206, Aug. 23, 1976, abandoned.

[51] Int. Cl.$^3$ ................................................ C08K 5/06
[52] U.S. Cl. ........................... 260/29.6 ME; 568/626; 568/666; 568/689
[58] Field of Search .................. 260/29.6 E, 29.6 ME; 526/209; 568/626, 666, 689

[56] References Cited

U.S. PATENT DOCUMENTS

| 2,239,515 | 4/1941 | Bartlett | 568/626 |
| 2,248,518 | 7/1941 | Stanley | 568/626 |
| 2,777,000 | 1/1957 | Shaw | 568/626 |

Primary Examiner—Paul R. Michl
Attorney, Agent, or Firm—J. Edward Hess; Donald R. Johnson; Patrick C. Baker

[57] ABSTRACT

In the acid-catalyzed etherification of olefins with alcohols, substantially complete recovery of alcohol and catalyst is obtained when small amounts of water (1-10%) are added to the reaction. The addition of water provides a two-phase reaction medium in which olefin and ether are in the upper phase and alcohol and catalyst are in the lower phase. These phases are maintained during the course of the reaction, which continues as a two-phase system. Certain novel ethers produced by this process are likewise disclosed herein.

2 Claims, 1 Drawing Figure

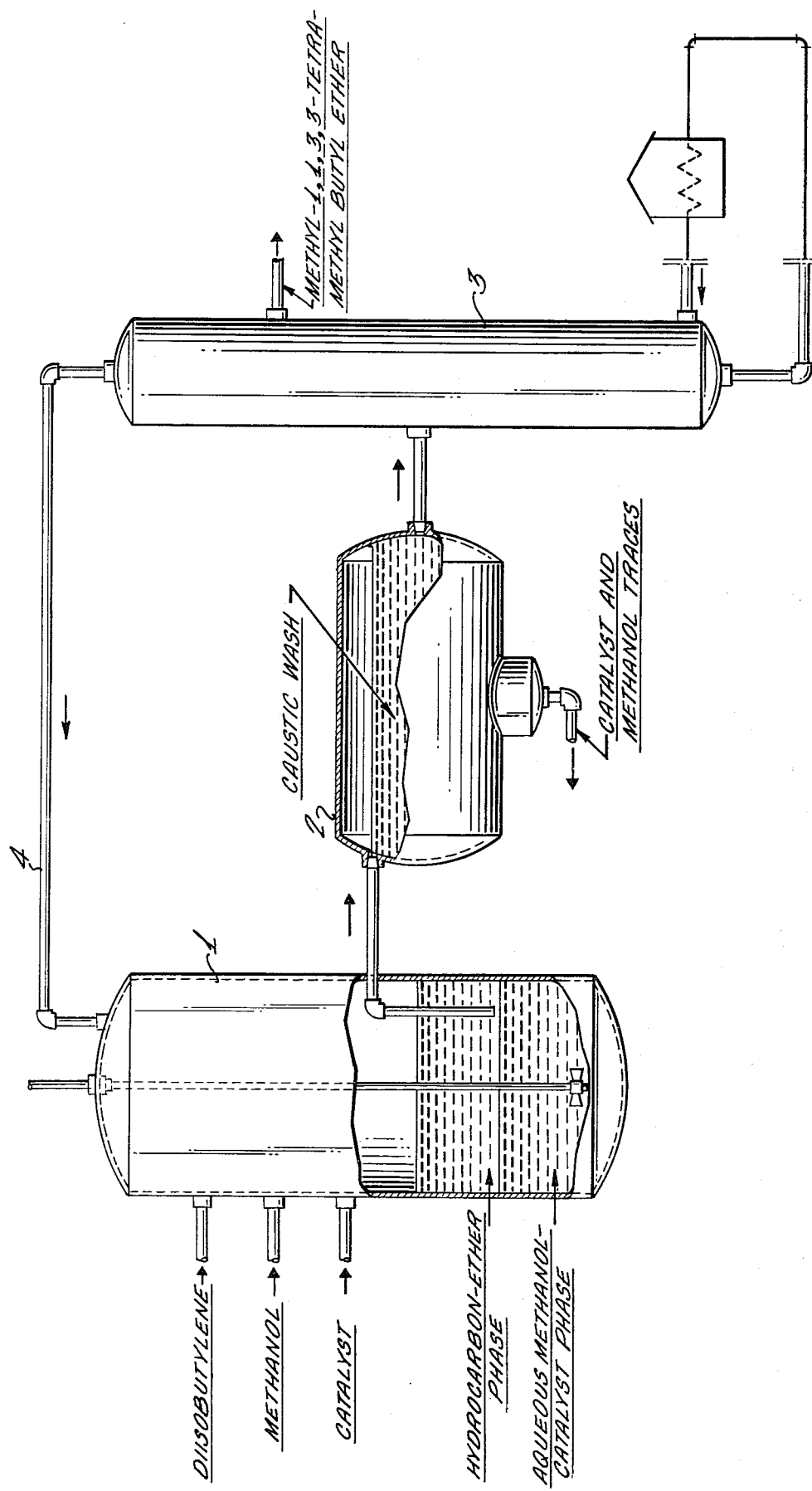

યુ4,292,219

LATEX-BASE PAINT CONTAINING 2-METHOXY-2-PHENYL PROPANE OR 8-METHOXY-P-MENTHANE

CROSS-REFERENCE TO RELATED APPLICATIONS

This is a division of application Ser. No. 863,569, filed Dec. 22, 1977, which in turn is a continuation-in-part of Ser. No. 714,206, filed Aug. 23, 1976, now abandoned, in the names of James F. Lyons and Peter Hosler.

Certain of the subject matter in this case is related to that of Ser. No. 658,435, filed Feb. 17, 1976, in the name of James E. Lyons, incorporated herein by reference, which discloses an alternate method of preparing one specific novel ether of the type prepared herein.

BACKGROUND OF THE INVENTION

This invention relates to certain novel ethers and to processes for the preparation of the same. In particular, this invention relates to an improved method for the continuous separation and recovery of products from reactants during the course of the reaction in the synthesis of ethers from branched olefins and alcohols in the presence of an acid catalyst.

The reaction of olefins with alcohols using acid catalysts such as p-toluene sulfonic acid to form ethers is known as shown, for example, in the aforementioned application, Ser. No. 658,435.

This earlier method, as in similar prior art methods, involves a homogeneous, single liquid-phase reaction in which, because of considerations of thermodynamic equilibrium, it is often necessary that large excesses of alcohol be present to maximize the yield. This, in turn, leads to a serious disadvantage in that these large amounts of alcohol must then be handled during recycling, together with unreacted olefin and catalyst, after separation of the ether product. This separation is generally accomplished by neutralizing the acid and water washing the alcohol from the organic phase before distilling the unreacted olefin from the product. The neutralization step, in turn, is undesirable because the acid catalyst is converted thereby to a less valuable salt, and distillation of the unreacted alcohol from the reaction medium is necessary for recycle.

Taken as a whole, then, this conventional, homogeneous, single-phase system is characterized by complicated and economically disadvantageous separation and recovery systems together with the handling of large volumes of excess alcohol.

In related art, W. Treibs, Berichte (1937), Vol. 70, pages 589–594, describes a process of preparing ethers from olefins and alcohols. Significantly, however, analysis of Treibs examples reveal that unlike applicant's process, as hereinafter described, said ethers are formed only when no water is present in the system. On the other hand, when Treibs example do describe hydrous systems, only alcohols corresponding to the olefin starting materials are recovered. By contrast, applicant's process does not yield alcohols.

SUMMARY OF THE INVENTION

In accordance with the present invention, it has now been found that, quite surprisingly, the foregoing processes can be substantially improved upon, and the disadvantages largely eliminated, by the addition of small amounts of water to the etherification reaction medium. By thus introducing sufficient amounts of water into the reaction system, there is obtained an essentially complete and continuous separation of the unreacted olefin and ether product into an upper phase, and the acid catalyst and excess alcohol into a bottom phase. By then continuously or periodically removing the upper phase, while the reaction is proceeding, recovery of the ether product is then greatly facilitated, while at the same time the handling of the acid and alcohol is eliminated since these reactants remain in situ in the reactor, or else are recovered as a single phase and returned to the reactor without the need for neutralization or distillation. This ready handling of the unreacted olefin is particularly advantageous in the case of those olefins having longer, higher molecular weight branch chains, since the tendency in those cases is for the equilibrium of the reaction to shift away from the product, and back towards the olefin starting material. In those cases, therefore it is economically imperative that these unreacted materials, which are present in larger volume than in the case of low molecular weight olefins, be recycled to the reactor. Using the present system, much, if not all, of this handling and recycling is thus avoided.

As a further advantage of the novel process, it has also been found that, surprisingly, the reaction rate is not greatly diminished despite the fact that the olefin and alcohol reactants are in two separate phases. Moreover, it is also surprising that despite the addition of water to the olefin and ether, selectivity in these systems remains extremely high and alcohol coproducts are not formed.

Certain novel ethers produced by this process which have not heretofore been described, are also claimed herein.

DESCRIPTION OF THE DRAWING

The drawing is a simplified schematic diagram illustrating one preferred embodiment of the invention as shown and described in Example 2.

DESCRIPTION OF THE INVENTION

The process of this invention, except for the novel features described above, comprises a conventional etherification reaction in which an olefin is reacted with an alcohol in the presence of an acid catalyst. The olefin may generally be defined as branched or cyclic mono-, di-, or tri-olefins having from 4 to 20 carbon atoms, as for example diisobutylene, dipentene, 2-methylpentene-2, α-pinene, α-methylstyrene and the like. The alcohol may be defined as a linear or branched $C_1$ to $C_{20}$ saturated alcohol, desirably such compounds as methanol, ethanol, propanol or butanol. The acid catalyst is desirably a sulfonic acid, such as p-toluene sulfonic acid, benzene sulfonic acid, or methane sulfonic acid, although other catalyst such as sulfuric acid, $BF_3$ etherate, hydrochloric acid, and phosphoric acid may likewise be employed. Of these, p-toluene sulfonic acid is preferred.

In carrying out this reaction the ratio of olefin to alcohol is desirably from 1:4 to 4:1 by volume and preferably 1:2 to 2:1. The amount of catalyst should be from 1 to 20% by weight of reactants, preferably 5 to 15%. The reaction is generally carried out at temperatures of from about 20° to 120° C., for a period of from about 0.5 to 70 hours, preferably 2 to 10 hours.

The amount of water added to the reaction medium to provide the unique two-phase system of this invention should be sufficient to form a two-phase system as described above, and in any event at least 1%, desirably from about 1–20% by volume, based on the amount of the total liquid volume of the reaction medium employed, and preferably from about 3 to 10%.

While the reaction may be carried out in a batch fashion, it will be understood, from the above description, that most advantageously the reaction should be conducted as a continuous process in which the upper phase containing the ether product and unreacted olefin is periodically removed, the product recovered, and the olefin recycled to the reactor together with fresh olefin feed. Makeup acid, alcohol, and water are then added to maintain the desired ratio of reactants.

The ether products of this improved process are generally known, and have utility in a wide range of industrial applications. Thus, for example, 2-methoxy-2-phenylpropane, 2-methoxy-2-methyl pentane and 2,6-dimethyl-2-methoxyheptane are useful as paint additives, high octane gasoline additives and solvents. In the case of methyl 1,1,3,3-tetramethylbutyl ether, this compound, as shown in earlier-filed application, Ser. No. 658,435 (supra), is useful, among other things, as a paint smoothing additive or as an octane-improving fuel component. The aforementioned 2-methoxy-2-phenylpropane, which may be prepared by reacting α-methyl styrene with methanol, is a particularly effective paint smoothing agent when combined with a commercial latex-based paint in amounts of from about 1 to 5 weight percent, preferably about 3 percent.

In a further embodiment of this invention, it has now been found that certain novel ethers may be produced by this process, which compounds are also useful as paint additives, octane-improving internal combustion engine fuel additives, industrial solvents, and the like. Thus, when 2,6-dimethyl-2-heptene is reacted with methanol, there is obtained 2,6-dimethyl-2-methoxyheptane, which is useful as a paint smoothing agent when incorporated into commercial latex paints in amounts of about 1 to 5%, preferably 3 weight percent. Likewise, reaction of diisobutylene with methanol provides ethyl isooctyl ether, also useful as an anti-foam and smoothing agent when combined with latex paints in amounts of about 3 weight percent. Other useful, novel ethers which may similarly be prepared include 2-methoxy-2-methyl-3-ethylhexane, formed by reacting 2-methyl-3-ethylhexene with methanol, and useful as a paint smoothing agent and a high octane fuel additive. Also, 8-methoxy-p-menthane may be prepared by first reacting methanol with either limonene, α- or β-pinene, then hydrogenating the reaction product, useful as a paint additive.

The foregoing inventions will now be illustrated by, although not limited, the following examples.

EXAMPLE 1

A mixture of 30 ml diisobutylene, 20 ml of methanol, 11 grams of p-toluene sulfonic acid and 5 ml of water were stirred for 24 hours at 60° C. After this time two layers had formed having the following composition: (g c of neutralized aliquots)

| | | |
|---|---|---|
| Top layer (29 ml) Diisobutylene | >84% | |
| methyl-1,1,3,3-tetramethylbutyl ether | ~15% | |
| methanol + water | <1% | |
| Bottom layer (27 ml) Diisobutylene | trace | |
| methyl-1,1,3,3-tetramethylbutyl ether | <1% | |

-continued

| | |
|---|---|
| methanol + water | >99% |

EXAMPLE 2

A mixture of 40 gallons of diisobutylene, 40 gallons of methanol, 80 pounds of p-toluene sulfonic acid and 1 gallon of water were stirred vigorously at 60° C. for 24 hours in glass lined reactor 1, fitted with stirrer, under nitrogen. After the phases had settled aliquots of each phase were neutralized with dry sodium carbonate. The top phase contained 81% diisobutylene, 19% methyl-1,1,3,3-tetramethylbutyl ether and ~1% methanol and water. The bottom phase contained <1% diisobutylene, <2% methyl-1,1,3,3-tetramethylbutyl ether and 97% aqueous methanol.

The stirrer was stopped and the top layer was the decanted, passed through to a caustic water wash 2 to remove traces of acid and methanol, then distilled in still 3 from a pad of hexadecane with added quinoline to insure that the medium be basic so that the ether product will not decompose during distillation. Unreacted diisobutylene (about 32 gal) was returned to the reactor through line 4 and the product, 1,1,3,3-tetramethylbutyl ether, 7.1 gallons, b. 290°–295° F., was isolated.

Diisobutylene (8 gal) and methanol (0.5 gal) were added to the reactor to approximate the original concentrations (40 gallons each). Reaction proceeded at 60° C. and after 24 hours approximately 19% of the top phase was again converted to methyl-1,1,3,3-tetramethylbutyl ether.

EXAMPLE 3

A mixture of 30 mls. of 2,6-dimethyl-2-heptene, 30 mls. of methanol, 6 grams of p-toluene sulfonic acid and 3.0 ml. of water were stirred at 60°–65° C. for 24 hours. After this time glpc analysis showed that the neutralized top layer contained nearly 17% 2,6-dimethyl-2-methoxyheptane. Distillation of the top layer gave a pure ether cut, 3.3 grams, which was shown to be 2,6-dimethyl-2-methoxyheptane by mass spectrometry: (α-cleavage to give fragments: $(CH_3)_2(CH_3O)C$, mass-73, 100%); its nmr spectrum: (3 protons at 3.1 ppm $(CH_3O)$, 6 protons at 1.1 ppm $(>C(CH_3)_2)$, its ir spectrum (absorption at 9.2μ (C—O) and its elemental analysis.

EXAMPLE 4

A mixture of 30 mls. of 2-methyl-3-ethylhexene-1, 30 mls. methanol, 6 grams of p-toluene sulfonic acid and 3.0 ml. of water were reacted in the manner of Example 3 to give 3 grams of ether which was shown to be 2-methoxy-2-methyl-3-ethylhexane by mass spectrometry: (α-cleavage to give $(CH_3)_2(CH_3O)C$ fragment, mass-73, 100% as well as ethyl and methyl fragments), its nmr spectrum: (3 protons at 3.1 ppm $(CH_3O)$, 7 protons at 1.3 ppm (br) $(CH_2$ and $CH)$, 6 protons at 1.1 ppm (s) $(>C(CH_3)_2)$, 6 protons at 0.9 (tr) $(CH_2CH_3)$, its ir spectrum (absorption at 9.2 (C—O) and its elemental analysis.

EXAMPLE 5

A mixture of 30 mls of 2-methylpentene-2, 30 mls of methanol, 6 grams of p-toluene sulfonic acid and 5 ml of water were stirred for 24 hours at 50° C. After this time two layers were present as in previous examples. The top layer was found to contain nearly a 60% yield of 2-methoxy-2-methylpentane. The entire reaction mixture (both phases) was neutralized by adding 120 mls of 10% sodium carbonate. Analysis by g c showed that 66% of the 2-methylpentene-2 had been converted to 2-methoxy-2-methylpentane.

EXAMPLE 6

A mixture of 16 mls of β-pinene, 16 mls of methanol, 3.2 grams of p-toluene sulfonic acid and 2.5 mls of water were stirred at 25° C. for 72 hours. After stopping the stirrer the two phases separated. The top, 12 mls, contained methanol, 20%, α+β-pinene, 8%, olefin isomers including limonene and camphene, 20%, and methylterpene ethers including endo- and exo-methyl-bornyl ether and limonene methyl ether totaling 52%. The bottom layer was over 90% methanol and a mixture of the olefins and ethers mentioned above in less than 10%. Analysis of the layers was performed by gas chromatography, the pure products isolated and identified by comparison of their ir and nmr spectra with authentic samples. The yield of limonene methyl ether in this reaction was 33%.

EXAMPLE 7

A mixture of α-pinene, 30 ml, methanol, 30 ml, p-toluene sulfonic acid, 6 grams, and water, 5 ml, was stirred at 56° C. for 4 hours. After settling two layers resulted: the top layer containing 28 ml and the bottom layer, 37 ml. Analysis as in Example 6 showed the top layer to contain methanol, 11%, α+β-pinene 21%, olefin isomers including camphene and limonene, 23% and ethers including methyl bornyl ether, methyl isobornyl ether, 2-methoxy isocamphane, 8-methoxy-p-menth-3-ene and 1,8-dimethoxy-p-menthane (45%). Of this mixture, 8-methoxy-p-menth-3-ene (limonene methyl ether) comprised 31% and the others totaled 14%. The bottom layer contained over 90% methanol and ~10% of a mixture of olefins and ethers.

EXAMPLE 8

In a manner similar to Example 7, limonene was reacted with methanol to form a mixture of terpene methyl ethers (51% yield) containing limonene methyl ether in 35% yield.

EXAMPLE 9

A mixture of diisobutylene, 30 ml, methanol, 30 ml and aqueous 40% HCl, 6 ml, were stirred at 63° C. for 3 hours. After this time stirring was stopped and the volumes of the resulting layers measured and analyzed. The top layer, 29 mls, contained 16.5% 1,1,3,3-tetramethylbutyl ether and 82% unreacted diisobutylene in addition to a small amount of 1,1,3,3-tetramethylbutyl chloride and a trace of methanol. The lower layer was over 99% methanol.

EXAMPLE 10

Limonene methyl ether (8-methoxy-p-menth-3-ene), 20 ml. in methylcyclohexane, 40 ml, was hydrogenated over platinum oxide (Adam's Catalyst) at 150 psi to give high yield, 8-methoxy-p-menthane having the formula

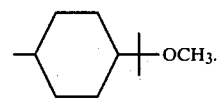

The invention claimed is:

1. A paint composition comprising a latex-base paint having incorporated therein from about 1 to 5 weight percent of 2-methoxy-2-phenylpropane as a paint-smoothing agent.

2. A paint composition comprising a latex-base paint having incorporated therein from about 1 to 5 weight percent of 8-methoxy-p-menthane as a paint-smoothing agent.

* * * * *